(12) United States Patent
Rainer

(10) Patent No.: US 7,591,588 B2
(45) Date of Patent: Sep. 22, 2009

(54) SUPPORT ARM FOR A CEILING HOLDER FOR AN X-RAY SOURCE

(75) Inventor: Häupl Rainer, Krummennaab (DE)

(73) Assignee: Siemens Aktiengesellschaft (DE)

( * ) Notice: Subject to any disclaimer, the term of this patent is extended or adjusted under 35 U.S.C. 154(b) by 0 days.

(21) Appl. No.: 10/798,203

(22) Filed: Mar. 11, 2004

(65) Prior Publication Data

US 2005/0008125 A1 Jan. 13, 2005

(30) Foreign Application Priority Data

Mar. 14, 2003 (DE) ................. 103 11 456

(51) Int. Cl.
*H05G 1/02* (2006.01)
(52) U.S. Cl. ...................................... 378/197
(58) Field of Classification Search .......... 378/195–197
See application file for complete search history.

(56) References Cited

U.S. PATENT DOCUMENTS

| | | | | |
|---|---|---|---|---|
| 3,784,837 A | * | 1/1974 | Holmstrom | ................. 378/189 |
| 4,501,011 A | * | 2/1985 | Hauck et al. | ................ 378/196 |
| 4,727,564 A | * | 2/1988 | Mekker et al. | .............. 378/197 |
| 4,901,339 A | * | 2/1990 | Heinz et al. | ................. 378/197 |
| 5,159,622 A | | 10/1992 | Sakaniwa et al. | |
| 5,636,259 A | | 6/1997 | Khutoryansky et al. | |
| 6,027,247 A | | 2/2000 | Tachi et al. | |
| 2002/0118793 A1 | * | 8/2002 | Horbaschek | ................ 378/197 |

FOREIGN PATENT DOCUMENTS

| | | |
|---|---|---|
| DE | U 8706822 | 5/1987 |
| DE | A 4 311 702 | 10/1994 |
| DE | A 4 325 526 | 10/1994 |
| EP | A 0 068 930 | 5/1982 |

OTHER PUBLICATIONS

Translation of DE 4325526.*
Translation of DE 4311702.*

* cited by examiner

*Primary Examiner*—Chih-Cheng G Kao
(74) *Attorney, Agent, or Firm*—Brinks Hofer Gilson & Lione

(57) ABSTRACT

A support system for an x-ray source comprises a support arm and a ceiling holder. The ceiling holder includes a substantially vertically adjustable mounting device. The support arm is secured to the mounting device. The x-ray source is secured, rotatably about a substantially horizontal axis, to the support arm. The substantially horizontal axis of rotation of the x-ray source is disposed above a lower edge of the mounting device and a lower edge of the support arm. Also, a height of the substantially horizontal axis is adapted to the x-ray source in such a way that the lower edge of the x-ray source, independently of the angle of rotation about the substantially horizontal axis, is disposed below the lower edge of the support arm and the lower edge of the mounting device.

7 Claims, 4 Drawing Sheets

SUPPORT ARM FOR A CEILING HOLDER FOR AN X-RAY SOURCE

BACKGROUND

The invention relates, generally, to a support system for a radiation system, and more particularly, to a support system for an x-ray source.

In medical radiological diagnostics, x-ray systems typically have an x-ray source, which may be disposed above a patient bed or above the patient. The patient bed may also be a cot, a table top, or gurney. Below the patient bed, on which the patient is placed, or behind the patient, an x-ray detector may be provided for recording x-rays that have penetrated or passed through the patient. The x-ray source may be mounted so as to be movable in all directions in space, i.e. in three dimensions. As such, the x-ray source can be used in versatile irradiation angles and positions, for instance with x-rays passing through the patient vertically or horizontally. To that end, the x-ray source may be mounted on the ceiling of an examination room using a ceiling holder. The x-ray source may also be mounted to a moveable x-ray system platform. The ceiling holder may be designed such that the x-ray source is adjustable in all three directions in space, so that desirable regions of the patient's body to be examined can be x-rayed. The ceiling holder is also rotatable, so that desirable directional angles can be achieved.

First, the three-dimensional movability of the x-ray source may be satisfied by providing that the ceiling holder is at least adjustable vertically. As such, the ceiling holder may have a mounting device or retaining device, having a telescoping mechanism. Second, the x-ray source may be secured to the mounting device or the telescoping mechanism via a support arm or support member of the ceiling holder. The support arm may be rotatable about the vertical axis of the mounting device, and the x-ray source is rotatable on the support arm about a horizontal axis. In addition, the mounting device can be secured to the ceiling of the examination room via a rail system, to allow for a horizontally desirable adjustment along an entire length of the patient bed.

Since the x-ray source may be substantially heavy or bulky, a plurality of the parts defining the ceiling holder may be dimensioned so as to be suitably massive. As such, considerable space may be taken up by a substantially bulky x-ray source and ceiling holder assembly. Moreover, mechanisms for supporting vertical motions of the x-ray source, in particular, may be provided so that an operator or user need not hold or lift the entire weight of the x-ray source along with the support arm and the mounting device. For supporting vertical motions, weight compensating devices, such as counterweights connected by cable, and under some circumstances involving even motors, are therefore provided. To improve a manual adjustability of the x-ray source, stable handles may also be provided, to facilitate, for instance, for the operator aiming of the x-ray source at body parts of the patient that are to be examined. All these mechanisms and components may contribute to a considerable spatial requirement of the overall x-ray system.

For a patient, to be examined, to experience a psychologically more favorable examination, the x-ray system in and under which he has to be placed may not be overly and oppressively massive. In addition, it is quite generally an advantage if the parts of the x-ray system are designed to be as space-saving as possible.

One possible way of increasing an available free space inside the x-ray system, for instance between the patient bed and the x-ray source together with the ceiling holder, is to design the support arm in such a way that the x-ray source can be moved upward as far as possible toward the ceiling of the room together with the mounting device. This design may increase the amount of free space between the patient bed and the moved up or raised x-ray source, and both the operator and the patient have more freedom of motion for placing and positioning of the patient. To achieve this design, the support arm may be given a shape that may be bent at a right angle as markedly upward as possible. As a result, an underside of the mounting device or of the support arm may form a lower edge of the entire assembly comprising the ceiling holder and the x-ray source, while vice versa the x-ray source may protrude no farther downward vertically than the ceiling holder. The vertical free space may then be limited at a top only by a maximum adjustability of the mounting device.

Now, however, for radiological examination of a patient, the x-ray source must be moved as close as possible to the patient, depending on the x-ray examination image or view to be taken. Typically, x-ray sources have so-called multileaf diaphragms (collimators), which can be moved to where they nearly touch the patient and thus predetermine a minimum spacing between the patient and the radiation generator. When x-ray examinations are made with such close spacing, all the edges of the ceiling holder may prove to be problematic or interfering, because they could come into contact with the patient. They can not only impair free movability but also hinder the minimum spacing between the x-ray source and the patient, if the patient is in the way of their motion or could even bump against them.

To avoid such problematic ceiling holder edges near the patient, the pronounced or exaggerated upward right-angle bend of the support arm may prove to be counterproductive. Instead and on the contrary, a substantially right-angle bend of the support arm in the downward direction may be necessary, so that the underside of the x-ray source may form the lower edge of the entire x-ray system. The movability of the x-ray source in an immediate vicinity of the patient to be examined is then restricted solely by the lower edge of the x-ray source.

A markedly downward right-angle bend of the support arm, however, may prove to be a hindrance to the above-explained upward adjustability of the x-ray system, which should be as great as possible, since the lower edge of the x-ray source is always located below the ceiling holder that is moved maximally upward and thus reduces a height of the room that remains available.

The support arms or members of conventional ceiling holders for x-ray systems have either a substantially upward right-angle bend or downward right-angle bend. Thus, in conventional ceiling holders, either a disadvantage of restricted upward adjustability and hence restricted vertical free space, or a disadvantage of pronounced problematic or interfering lower edges near the patient was accepted and incorporated into the design of the x-ray system.

OBJECT AND SUMMARY

The present invention is defined by the following claims. This description summarizes some aspects of the present embodiments and should not be used to limit the claims.

An object is to disclose a support arm for a ceiling holder of an x-ray system which on the one hand minimizes the problematic lower edges close to the patient and on the other hand assures the greatest possible upward adjustability and the greatest possible vertical available free space.

One concept is a support arm which has an only slight upward right-angle bend. The right-angle bend of the support arm is adapted to the x-ray source in such a way that the lower edge of the x-ray source, regardless of the x-ray source spatial orientation, is located at all times below the ceiling holder. In particular, regardless of the x-ray source angle of rotation with respect to a rotation about the horizontal axis, the lower edge of the x-ray source is always located below the lower edge of the support arm and the lower edge of the mounting device or telescoping mechanism. At the same time, a height of the right-angle bend assures that the horizontal axis about which the x-ray source is rotatable is located above the connection between the support arm and the mounting device.

Thus, the lowest edge, close to the patient, of the assembly comprising the ceiling holder and the x-ray source is substantially defined by the lower edge of the x-ray source, while any other potentially problematic edges are receded upward. Because there is still a right-angle bend of the support arm in the upward direction, the assembly comprising the ceiling holder and the x-ray source is adjustable as far as possible upward and allows the greatest possible vertical free space, sandwiched between the assembly and the patient bed below.

In an advantageous feature, the horizontal axis about which the x-ray source is rotatable on the support arm extends laterally past the mounting device. In that case, the x-ray source is disposed not in a symmetrical position on the ceiling holder but rather on a lateral side of the ceiling holder at approximately near the upward bend portion of the support arm. As a result, in x-ray views in which the x-ray source is positioned laterally of the patient so that the x-rays pass through him from the side, the problematic edges are reduced substantially, since the x-ray source is not only rotated toward the patient but is also inclined away from him.

In another advantageous feature, the horizontal axis about which the x-ray source can rotate on the support arm extends laterally of the mounting device at a spacing adapted to the x-ray source in such a way that a linear extension of one of two side edges of the x-ray source extends parallel to the horizontal axis with substantial spacing from the mounting device, while the corresponding linear extension of the other and opposite side edge extends either through or past the mounting device on the opposite side. As a result, the side edges of the x-ray source in the horizontal direction always form the edge that comes closest to the patient, while the side edges of the mounting device that are problematic edges do not protrude substantially past the side edges of the x-ray source.

Further advantageous features are the subject of the dependent claims.

Exemplary embodiments of the invention are described in further detail below in conjunction with the drawings.

DESCRIPTION OF THE PREFERRED EMBODIMENTS

Figure 1:
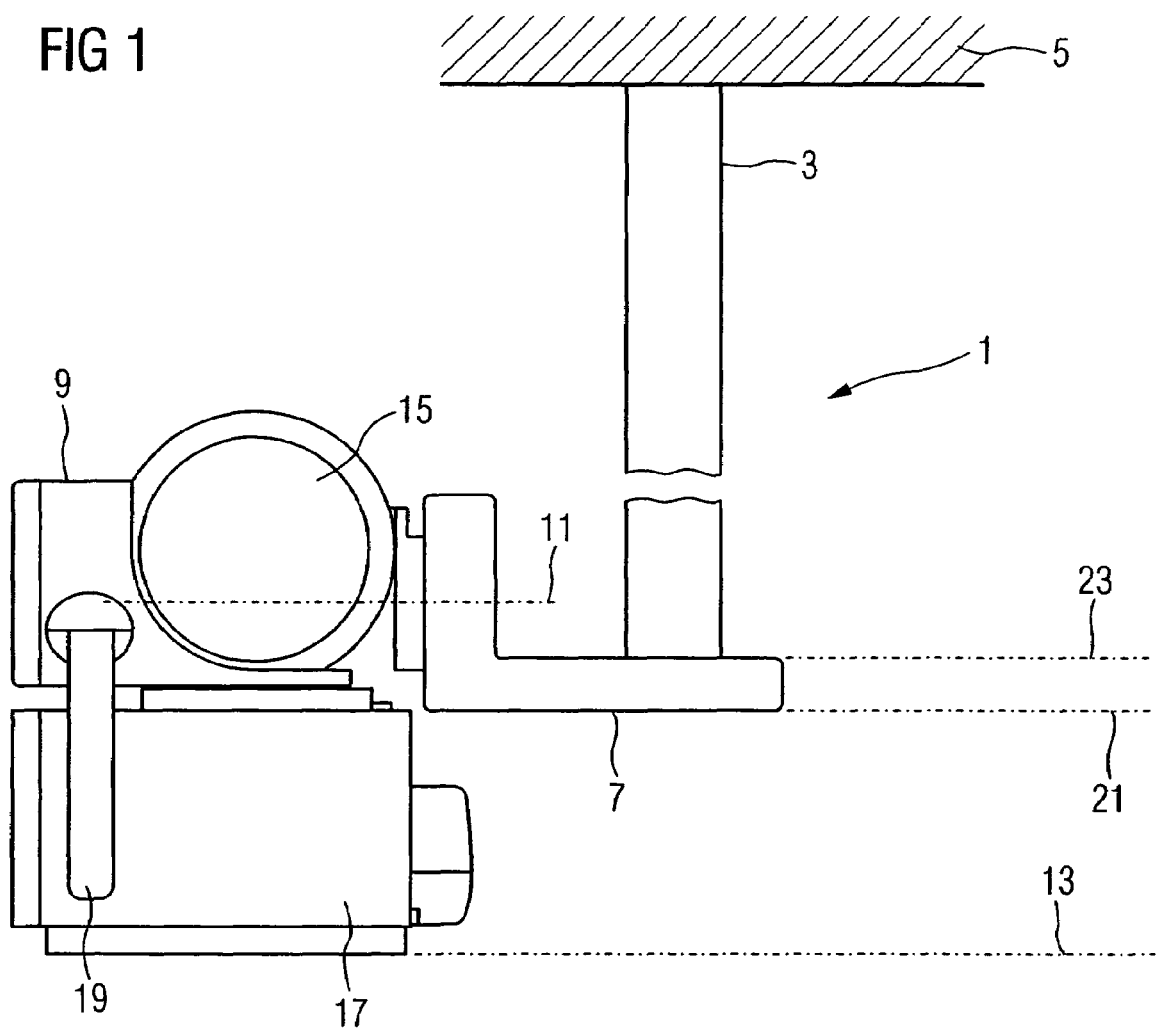
FIG. 1 is a side view of a ceiling holder with a support arm with an upward right-angle bend.

In FIG. 1, a preferred embodiment of the ceiling holder 1 is shown from a side view perspective. The ceiling holder 1 comprises a mounting device 3, which is vertically oriented and is variable in its length. A mechanism for varying the length of the mounting device 3 is not shown in the drawing; for instance, a telescoping mechanism could be employed. The mounting device 3 is secured to the ceiling 5 of the room in which the entire x-ray system is located. A support arm 7 is secured to the underside of the mounting device 3.

The support arm 7 has an upward right-angle bend part. The part of the support arm 7 that is bent upward at a right angle, as shown in FIG. 1, supports an x-ray source 9. The x-ray source 9 is disposed rotatably about a horizontal axis 11 on the support arm 7; the axis 11 is merely an imaginary axis of rotation, and no actual fastening device is shown in FIG. 1.

The x-ray source 9 comprises an x-ray generator 15, such as an x-ray tube, and a multileaf diaphragm 17, whose diaphragm system specifies a format and extent of an x-ray beam generated. At the same time, the multileaf diaphragm 17 serves to assure a minimum spacing between the x-ray generator 15 and a patient, not shown in the drawing and who is to be examined, in the event that the x-ray source 9 is moved until contact is made with the patient. The x-ray source 9 may be relatively heavy, not least because of a housing structure designed as a shield against x-radiation, and may accordingly require considerable force to move. To make the x-ray source easier for an operator to adjust or move, the x-ray source therefore has a stable, massive handle 19, which can be grasped with an entire hand.

Movements of the x-ray source 9 could also be made easier, or could be executed, by servo motors. In addition, weight compensating devices, such as springs or compensating weights connected by cable, can be provided. Such mechanisms are not shown in the drawing, however.

At the angle of rotation shown for the x-ray source 9 about the horizontal axis 11, an x-ray beam points vertically downward. This beam is generated by the x-ray generator 15 and passes through the multileaf diaphragm 17, which can for instance contact with or bump against a patient's body that is to be examined. That is, the patient's body to be examined is placed vertically beneath the assembly, and the lower edge 13 of the x-ray source, and of the multileaf diaphragm 17 for the current angle of rotation, may come spatially closest to that patient's body. This edge 13, used for close-up x-ray views or images, is intended for mutual contact with the patient's body to be examined and in that sense cannot be considered a problematic edge. The lower edge 21 of the support arm 7, whose spacing is of not importance to the creation of x-ray views, however, may be a problematic edge. The lower edge 21 remains substantially behind or above the edge 13 of the multileaf diaphragm 17. As the ceiling holder 1 is adjusted and the patient to be examined is being aimed at with the x-ray source, this lower edge 21 is therefore no hindrance, and a probability that the patient be bumped against is low.

However, the right-angle bend of the support arm 7 points so far upward that the diaphragm lower edge 13 of the x-ray source 9, when the mounting device 3 is moved maximally upward, may slightly as possible protrude downward along a vertical. Compared to a support arm without a right-angle bend, the downward protrusion is essentially offset upward by the height of the upward right-angle bend and makes a corresponding height in the room free; this space is available for instance for the patient to be examined, for additional space in which he can move or be moved freely, be placed and positioned on the patient bed, not shown,. That is, the height of the right-angle bend is adapted to the height of the x-ray source 9. Because of the increased vertical space that remains free or open, the room height required to accommodate the x-ray system can be selectively reduced by a height dimension of the right-angle bend of the support arm. This makes the x-ray system correspondingly more versatile to use.

The height of the right-angle bend is characterized in that the lower edge 13 of the x-ray source 9 is disposed below the lower edge 21 of the support arm 7 and the lower edge 23 of the mounting device 3, where the connection between the support arm 7 and the mounting device 3 is located, and is thus closer to the patient than all the problematic edges of the ceiling holder 1. A further characteristic is that the horizontal axis 11, about which the x-ray source 9 is rotatable, is disposed above both the lower edge 21 of the support arm 7 and the lower edge 23 of the mounting device 3.

Figure 2:
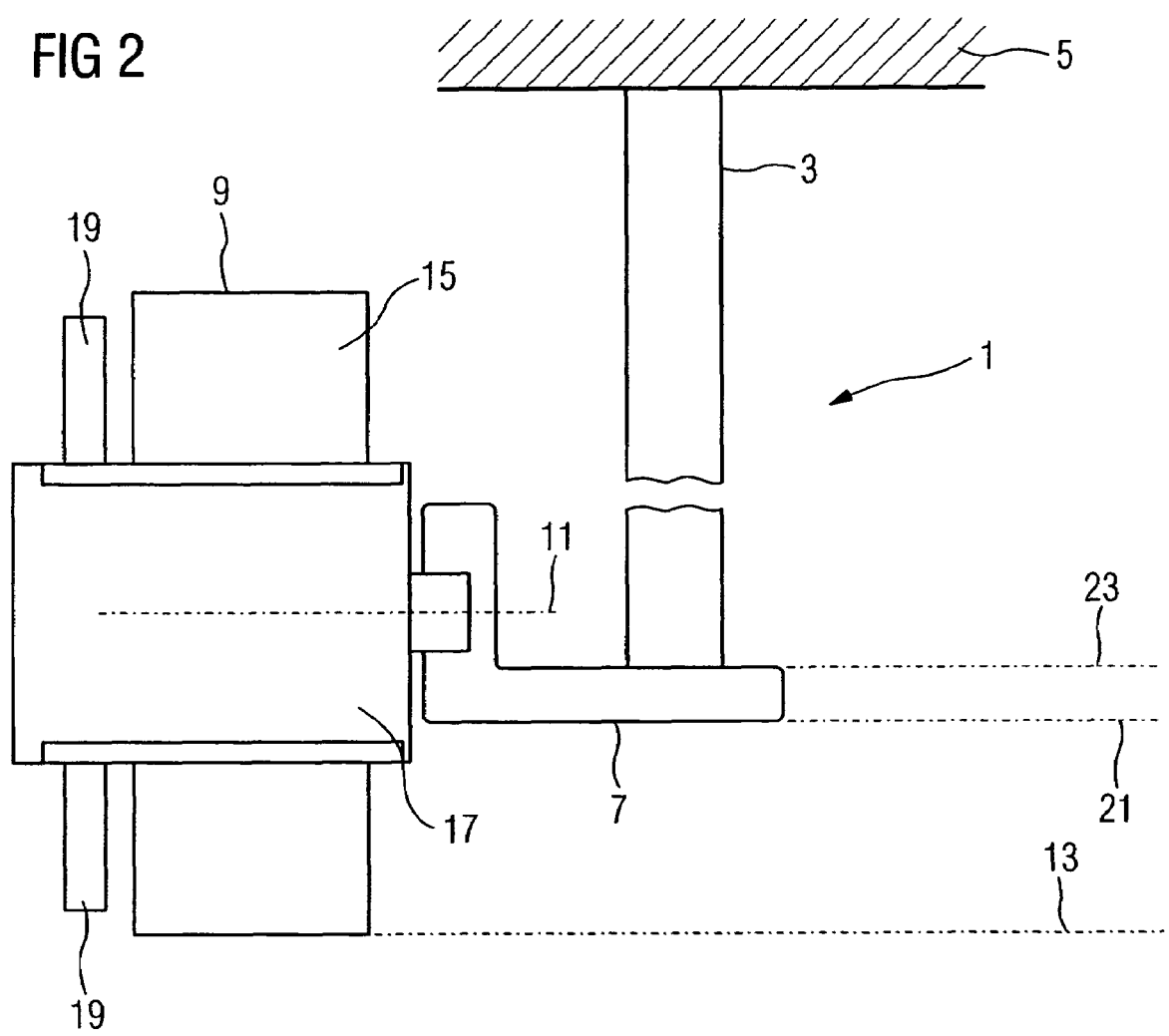
FIG. 2 is a side view arm with an upward right-angle bend and a rotated x-ray source.

In FIG. 2, the ceiling holder assembly described above, comprising the ceiling holder 1 and x-ray source 9, is shown with an angle of rotation of about 90° about the horizontal axis 11 from the vertical. The other parts of the x-ray system are unchanged compared to the perspective view of FIG. 1 as described above, and so the same reference numerals will be used for them. Because of the altered orientation of the x-ray source 9, one can see that the x-ray source 9 has two handles 19 for manual adjustment, each one located namely at one point on each side.

It can be seen clearly from the drawing of FIG. 2 that because of the upward right-angle bend of the support arm 7, the lower edge 13 of the x-ray source 9, regardless of its angle of rotation, is located below the lower edge 21 of the support arm 7 and the lower edge 23 of the mounting device 3. As a result, one can clearly see that the x-ray source 9, at an arbitrary angle of rotation about the horizontal axis 1, is always located lower, and hence closer to the patient placed beneath the x-ray source 9, than any problematic edge of the ceiling holder 1.

Figure 3:
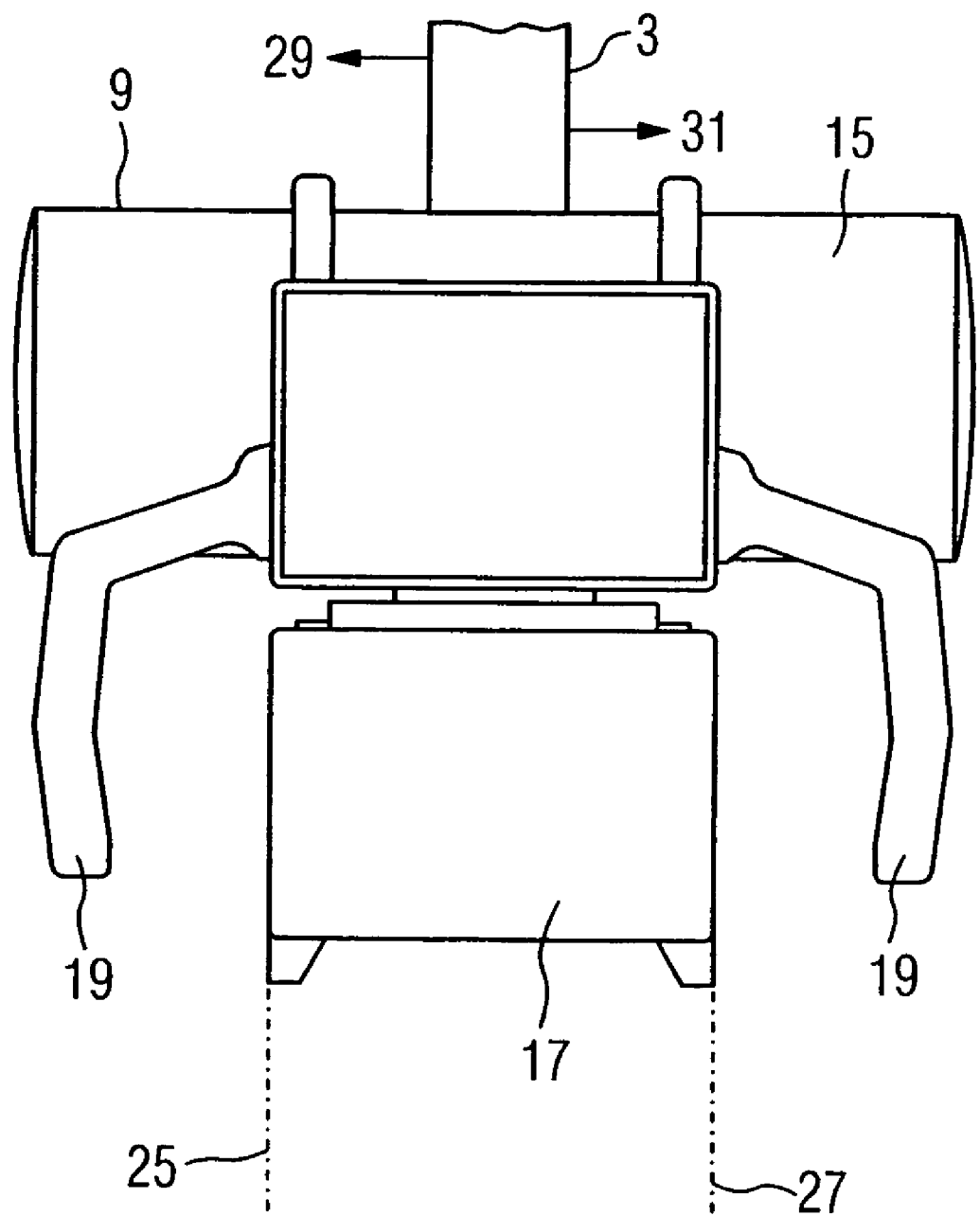
FIG. 3 is a front view of a ceiling holder with a support arm with an upward right-angle bend.

In FIG. 3, the same assembly comprising the ceiling holder 1 and x-ray source 9 is shown as in the previous drawings, but in a plan view perspective. The same x-ray system parts are shown, using identical reference numerals, but now the shape of the handles 19 is shown more clearly.

In this plan view perspective, side edges 25 and 27 of the x-ray source 9 can be seen; they are oriented essentially parallel to the horizontal axis 11, which is not shown. The side edge 25 is located on the left in FIG. 3, in a side region 29 laterally of the mounting device 3. The side edge 27 is located on the right in FIG. 3, in another side region 31 laterally of the mounting device 3. In this variant view of the ceiling holder 1 as shown, the support arm 7 which according to the invention has an upward right-angle bend, is shown in this lateral orientation to be symmetrical with respect to the mounting device 3. That is, the support arm is not bent laterally at a right angle.

Figure 4:
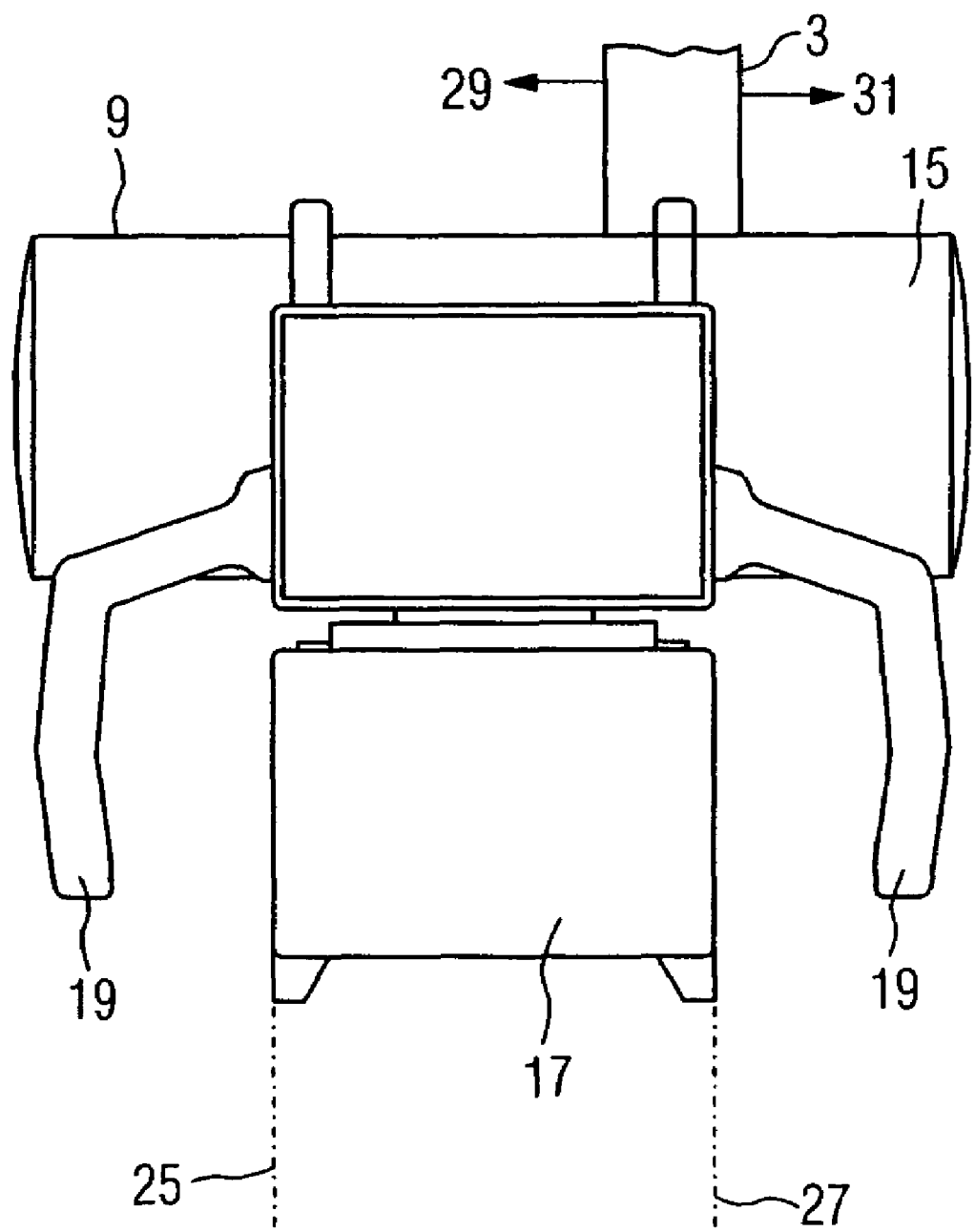
FIG. 4 is a front view of a ceiling holder with a support arm with an upward and sideward right-angle bend.

In FIG. 4, a ceiling holder 1 with an x-ray source 9 is shown in the same view as in FIG. 3, and identical reference numerals are used for the parts of the x-ray system. However, the support arm 7, which in this view is concealed by the x-ray source 9, has in addition to the upward right-angle bend a lateral or sideward right-angle bend, which is adapted to the width of the x-ray source 9 and by which the horizontal axis 11 is laterally deflected. As a result, in terms of the side edges 25 and 27, the x-ray source 9 is not disposed symmetrically with respect to the mounting device 3. The lateral deflection is adapted to the x-ray source 9 in such a way that the side edge 25 is displaced farther to the side of the mounting device 3 in the region 29 on the left, while the side edge 27 is located frontally before the mounting device 3.

The lateral right-angle bend of the support arm 7 according to the invention is characterized in that the mounting device 3 is located either between the side edges 25 and 27 of the x-ray source 9 or in the region frontally after one of the two side edges 25, 27. As a result, one can be assured that the edges of the mounting device 3 that would be problematic to the patient are at a greater spacing from the patient than the side edges 25, 27 of the x-ray source 9. As a result, a substantially improved movability of the x-ray source 9 with simultaneous minimization of the probability that the patient comes in contact with the problematic or interfering edges is assured.

Alternatively, the x-ray source 9 may also be mounted to or affixed to a supportive platform other than a ceiling. The supportive platform may also be moveable.

What is claimed is:

1. A support system for an x-ray source, comprising:
   a ceiling holder including a mounting device; and
   a support arm fixedly secured about a horizontal axis to the mounting device, such that the x-ray source is secured, rotatably about a substantially horizontal axis, to the support arm;
   wherein a lower edge of the mounting device and a lower edge of the support arm are disposed vertically below the horizontal axis of rotation of the x-ray source; and
   wherein the horizontal axis of rotation of the x-ray source is positioned on the support arm such that a portion of an envelope of the x-ray source remains below the lower edge of the support arm and the lower edge of the mounting device independently of the angle of rotation about the horizontal axis of rotation; and a line extension of the horizontal axis of rotation of the x-ray source is laterally displaced with respect to a vertical axis of symmetry of the mounting device.

2. The support system for an x-ray source of claim 1, wherein the support arm comprises a substantially right angled bend.

3. The support system for an x-ray source of claim 1, wherein the support arm is fixedly secured about a vertical axis to the mounting device.

4. The support system for an x-ray source of claim 1, wherein the mounting device is substantially vertically adjustable.

5. The support system for an x-ray source of claim 1, wherein the ceiling holder is rotatable about a substantially vertical axis.

6. The support system for an x-ray source of claim 1, wherein the line extension of the horizontal axis of rotation of the x-ray source is parallel to lines extending along each of two side edges of the x-ray source; and
   wherein one of the lines of one of the two side edges of the x-ray source extends on one vertical side of the mounting device and the other line of the other side edge extends on another vertical side of the mounting device.

7. A support system for an x-ray source, comprising:
   a ceiling holder including a mounting device; and
   a support arm fixedly secured about a horizontal axis to the mounting device, such that the x-ray source is secured, rotatably about a substantially horizontal axis, to the support arm,
   wherein a lower edge of the mounting device and a lower edge of the support arm are disposed vertically below the horizontal axis of rotation of the x-ray source;
   wherein the horizontal axis of rotation of the x-ray source is positioned on the support arm such that a lower edge of the x-ray source is disposed below the lower edge of the support arm and the lower edge of the mounting device, independently of an x-ray source angle of rotation about the horizontal axis; wherein a line extension of the horizontal axis of rotation of the x-ray source is laterally displaced with respect to a vertical axis of symmetry of the mounting device, and is parallel to lines extending along each of two side edges of the x-ray source; and wherein one of the lines of one of the two side edges of the x-ray source extends on one vertical side of the mounting device, and the other line of the other side edge extends through the mounting device.

* * * * *